US009326942B2

(12) United States Patent  (10) Patent No.: US 9,326,942 B2
Ciocca et al.  (45) Date of Patent: May 3, 2016

(54) MEDICAMENT, PARTICULARLY AN ANTI-CANCER MEDICAMENT, FOR TREATMENT USING IMMUNOTHERAPY, PARTICULARLY AUTOLOGOUS

(75) Inventors: Daniel Ciocca, Mendoza (AR); Patrick Frayssinet, Saint Lys (FR); Nicole Rouquet, Toulouse (FR)

(73) Assignee: URODELIA, Saint Lys (FR)

( * ) Notice: Subject to any disclaimer, the term of this patent is extended or adjusted under 35 U.S.C. 154(b) by 1096 days.

(21) Appl. No.: 11/914,295

(22) PCT Filed: May 15, 2006

(86) PCT No.: PCT/EP2006/062296
§ 371 (c)(1),
(2), (4) Date: Jun. 29, 2008

(87) PCT Pub. No.: WO2006/122914
PCT Pub. Date: Nov. 23, 2006

(65) Prior Publication Data
US 2009/0214585 A1  Aug. 27, 2009

(30) Foreign Application Priority Data
May 13, 2005 (FR) .................................... 05 51262

(51) Int. Cl.
*A61K 9/14* (2006.01)
*A61K 39/00* (2006.01)

(52) U.S. Cl.
CPC .............. *A61K 9/143* (2013.01); *A61K 39/0011* (2013.01)

(58) Field of Classification Search
None
See application file for complete search history.

(56) References Cited

U.S. PATENT DOCUMENTS 5,443,832 A * 8/1995 Amerongen et al. ...... 424/278.1
6,410,027 B1 * 6/2002 Srivastava ................ 424/193.1
6,541,000 B1   4/2003 Amerongen et al.
7,157,089 B1 * 1/2007 Mizzen et al. ............. 424/192.1
2002/0176845 A1 * 11/2002 Falkenberg et al. ........ 424/85.1
2003/0082232 A1   5/2003 Lee et al.

FOREIGN PATENT DOCUMENTS

| DE | 3426049 | 3/1986 |
| FR | 2543439 | 10/1984 |
| JP | 59197595 | 11/1984 |
| WO | 9835562 | 8/1998 |
| WO | 2004060407 | 7/2004 |

OTHER PUBLICATIONS

Saleem et al (J Controlled Release, 2005, 102:551-561.*
Wang et al, Int J Cancer, 2003, 105:226-231.*
Humphrey et al, J Surg Oncol, 1984, 25:303-305.*
Laquerriere et al, Biomaterial, 2003, 24:2739-2747.*
Paul, W. et al., Development of Porous Spherical Hydroxyapatite Granules: Application Towards Protein Delivery, Journal of Material Science, 1999, pp. 383-388, vol. 10, No. 7.
International Search Report, European Patent Office, mailed Nov. 17, 2006.
International Preliminary Report on Patentability (English translation), European Patent Office, mailed Nov. 17, 2006.

* cited by examiner

*Primary Examiner* — Mark Halvorson
(74) *Attorney, Agent, or Firm* — McAndrews, Held & Malloy Ltd.; Nabeela Rasheed

(57) ABSTRACT

The invention relates to a medicament characterized in that it comprises at least one solid biocompatible support, preferably in powder form, on which at least one active substance, preferably selected among biological materials and/or biological molecules, is adsorbed or on which it is to be adsorbed, preferably without requiring a coupling agent. Said solid biocompatible support is capable of purifying the active substance. The invention relates to also relates to a method for preparing a medicament of the aforementioned type, this method essentially consisting of placing at least one solid biocompatible support, preferably in powder form, in contact with at least one active substance, preferably selected among biological materials and/or biological molecules, in such a manner that the active substance is reversibly adsorbed and without denaturing on the support.

6 Claims, 5 Drawing Sheets

WESTERN BLOT- GP96

Fractions of 200

Figure 1:
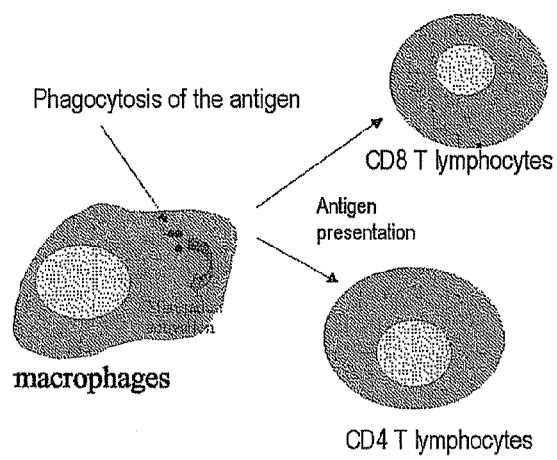

MEDICAMENT, PARTICULARLY AN ANTI-CANCER MEDICAMENT, FOR TREATMENT USING IMMUNOTHERAPY, PARTICULARLY AUTOLOGOUS

This application is a national phase application under 35 U.S.C. 371 of International Application No. PCT/EP2006/062296, filed May 15, 2006, which claims priority to FR 05/51262, filed May 13, 2005, the contents of which are hereby incorporated by reference.

FIELD OF THE APPLICATION

The field of the invention is that of immunotherapy treatments, in particular treatments for cancers, for infectious diseases or for autoimmune diseases, and means which are associated therewith.

More specifically, the invention relates to autologous treatments using immunostimulation. Even more specifically, the invention relates to means for combating in particular cancer, comprising antitumor vaccines obtained from the tumor antigens of patients.

The present invention relates in particular to a medicament, for example an antitumor vaccine, based on biocompatible mineral (e.g. hydroxyapatite) or polymeric microparticles.

The invention also relates to a method for preparing tumor antigens, intended to provide them in a form that is recognizable by the immune system, and more particularly for purifying the tumor antigens of a given patient in order to perform an autoimmunization generating a specific immune response against the tumor cells of the patient.

PRIOR ART

There are currently three types of forms of treatment against cancer using immunotherapy:

I. —Administration of Pharmacology Substances which Increase the Immune Response Nonspecifically.

This may, for example, involve the administration of interleukins or of interferon to patients who have a malignant renal tumor or alternatively a melanoma. Another nonspecific therapy is the administration of BCG in patients with a bladder cancer. These therapies have a varying degree of toxicity and, although they may show a certain amount of effectiveness, many patients treated in this way respond weakly. These therapies cause an amplification of many immune functions.

II. —Use of Specific Antibodies Against the Tumor Antigens Present at the Surface of the Tumor Cells.

One of the examples is the administration of monoclonal antibodies against the HER-2/neu oncoprotein. This oncoprotein is expressed in a low percentage (20-30%) of patients with breast cancer. The monoclonal antibody has been modified by genetic engineering so that only a small part of the molecule is of nonhuman origin (the part recognizing the antigen is produced by the rat), the rest of the molecule being of human origin. It is in fact a humanized hybrid antibody. Various hybrid antibodies have been produced, and have been evaluated, and some are used clinically in the treatment of various types of malignant tumors. The binding of the antibodies to their specific antigen leads the tumor cell to slow down its proliferation and brings about its death. Although these treatments are a significant advance, their effectiveness is limited due to the antigenic variability of tumor cells. In a solid tumor, at the moment of diagnosis, there are millions of tumor cells and, among this population, there are some cells which express the antigens of interest and others which do not.

III. —Stimulation of T Cells.

This form of therapy relates to the subject of the invention. Type III comprises adoptive immunotherapy, thus named since it is not innate, it develops away from the patient (ex vivo), with the aim of increasing the number of antitumor T cells. This is obtained by administering to the patient cytotoxic T cells which have been generated and amplified in vitro.

Type III also encompasses active immunotherapy based on the stimulation of T cells. This occurs by virtue of the tumor antigens being brought into contact with macrophages or related cells (such as, for example, dendritic cells of the skin: Langerhans cells), which present the antigens so that these cells, known as APCs (antigen-presenting cells), stimulate T lymphocytes. This strategy can be carried out in vivo or in vitro. These APCs initiate more than they maintain the specific antitumor immunity derived from the T lymphocytes. Active immunotherapy is the subject of numerous research studies for various tumors.

These agents for stimulating T lymphocytes can be compared to vaccines. Thus, several strategies A/, B/, C/, D/ exist for generating vaccines for stimulating the T system in active and specific form:

A/ Immunotherapy strategy based on the use of dendritic cells and other cells (in vitro). When they are in the growth phase, they are brought into contact, outside the organism, with the patient's tumor antigens (autologous tumor lysate, irradiated tumor cells, specific tumor peptides) and are injected intradermally into the same patient (the remainder are cryopreserved for other injections).

B/ Immunotherapy strategy based on the use of specific antigens and of stimulating molecules. There are numerous specific tumor antigens that may be used in vaccines, for example peptides produced from mutated genes, such as ras, p53 or VHL, which are combined with adjuvants such as Montanide ISA 51. It is also possible to use soluble synthetic or recombinant peptides of fractions of specific tumor antigens such as MART-1 (melanomas) or PSA (prostate).

C/ Immunotherapy strategy based on the use of tumor cells or of a tumor cell lysate. The tumor cells used in this strategy may be autologous or allogenic cells inactivated in various ways (radiation, freezing, heat, ultraviolet light), or else tumor cell lysates (the cells are homogenized).

D/ Immunotherapy strategies based on the use of heat shock proteins as adjuvant:

In this case, heat shock proteins (HSPs) such as gp 96 or HSP 70 are extracted from the tumor. These proteins act as molecular chaperons and transport peptides (antigens) specific for the tumor of each patient.

The ability of HSPs to bind to virtually the entire cellular proteome makes these molecules a good option as antitumor immunization, for three main reasons:

There is no need to know the entire tumor proteome since purification of the HSPs alone makes it possible to isolate a large number of proteins which are bound thereto.

Injection of said HSPs makes it possible, in a single step, to introduce into the organism a large amount of tumor proteins in a form that can be recognized by the immune system.

The HSPs allow the uptake, transit and remodeling of the proteins which are associated therewith by antigen-presenting cells so as to be presented to T lymphocytes.

One of the features of the use of these proteins as antitumor vaccine is the need to use HSPs originating from the tumor to be eradicated, since they constitute a molecular footprint of said tumor and differ from one patient and from one tumor to the other.

This means that the immunizing proteins must be purified from each tumor against which they must immunize the patient. The purification protocol is long, difficult to industrialize and subject to multiple contaminations with endotoxins. It is conventional to purify the HSPs from ground tumor material which is subjected to a series of centrifugation, precipitation, chromatography on Con A, electrophoretic analysis and chromatography on Mono Q FPLC.

U.S. Pat. Nos. 6,447,781, 6,436,404, 6,410,028, 6,383,494 and 6,030,618 describe methods for purifying HSPs consisting in using Con A Sepharose chromatographic columns. These methods can be improved.

Methods of purification which make use of calcium phosphates, and in particular hydroxyapatite (HA), are, moreover, known. Hydroxyapatite powders have been used for about thirty years to purify various biological molecules such as proteins, nucleic acids, endotoxins and even viruses. The powders are used as a fixed bed in chromatography columns through which the solution containing the molecule(s) to be purified is percolated. These molecules bind to the surface of the powder particles, from where they are desorbed with various concentrations of saline solutions such as phosphate buffers or sodium chloride, which makes it possible to separate the various molecules of the solution by means of gradients of phosphate buffers or the like.

HA ceramics in porous forms have also been used for about twenty years as a bone substitute. They are integrated into the bone tissue according to a sequence of biological events which follow on from one another and which can be listed as follows:
  Invasion of the pores by circulating cells.
  Colonization by a loose connective tissue.
  Formation of osteoid tissue at the surface of the material and mineralization.
  Remodeling of bone formed and degradation of ceramics.

Patent application US 2003/0082232 describes the use of a calcium phosphate-based, and in particular hydroxyapatite-based, support as an adjuvant and vector for vaccines, optionally in combination with an active agent, this active agent being a compound having been subjected to a purification treatment. Among the active agents mentioned, the following will be noted: purified proteins (for example: cytokine (GM-CSF or granulocyte macrophage-colony stimulating factor), purified diphtheria and tetanus toxins, keyhole limpet hemocyanin, dust, the deactivated human HIV-2 virus, a plasmid expressing a protein of *Plasmodium yoelii* (PyCSP), a bacterium (*Bordetella pertussis*) or alternatively a vaccine. The addition of active agent(s) to the calcium phosphate-based adjuvant preparation is always carried out with purified compounds, said purification being carried out using a protocol that does not use a calcium phosphate-based support.

One of the essential objectives of the invention is to simplify the method for improving tumor antigens intended to provide them in a form that can be recognized by the immune system in order to be able to apply it on a large scale using personnel who are not qualified biochemists.

To achieve this objective, it is to the inventors' credit that they have developed a method of preparation from the ground tumor material in a single step, which makes it possible to provide a vaccine on a vector material. This material allows at the same time the purification, the vectorization in the organism and the transport of the active substances into the target cells: antigen-presenting cells (APCs).

To achieve this objective, it is to the inventors' credit that they have demonstrated the advantage of certain biocompatible microparticulate mineral supports capable of adsorbing biological materials and/or molecules of interest with the aim of separating the molecules and vectorizing them.

Another essential objective of the invention is to provide a new immunotherapy (for example, autologous immunotherapy) medicament for the treatment of cancers, infectious diseases or autoimmune diseases, inter alia.

Thus, the invention relates to a method for preparing tumor antigens intended to provide them in a form that can be recognized by the immune system, characterized in that it consists essentially in:
  using a tumor extract,
  bringing this tumor extract into contact with a particulate mineral support capable of selectively adsorbing the targeted tumor antigens and in vectorizing them in vivo as substances that are active on the immune system,
  seeing to it that the particulate mineral support selectively adsorbs the tumor antigens of interest,
  separating the mineral support from the nonadsorbed tumor extract so as to collect the tumor antigens of interest in a form that is purified and adsorbed onto the support.

The method according to the invention advantageously comprises an additional step of mixing the tumor antigens that have been purified and adsorbed onto the support, with at least one cofactor capable of promoting the action of the tumor antigens on the immune system, said cofactor preferably being derived from tumor extracts, in particular from ground materials, lyophilizates, dialysates or a centrifugation pellet.

The cofactor, for its part, advantageously originates at least in part from the tumor extract, and even more particularly from the extract from which the targeted tumor antigens were purified by adsorption onto the particulate mineral support. This cofactor is even more advantageously chosen from cytokines, interleukins, growth factor or interferon, or a mixture thereof.

It should be noted that the means and the method according to the invention make it possible to remove the tumor factors that may lead to side effects.

In a specific embodiment of the invention, the method for preparing the tumor proteins comprises the following steps:
  preparing the tumor extract allowing the suspension or the solubilization of the tumor antigens of interest,
  percolating said suspension or solution through at least one column containing the particulate mineral support,
  washing the column with buffer solutions of given ionic strength and given pH,
  collecting the support that has adsorbed the tumor antigens.

The column washing step makes it possible to separate the mineral support from the tumor extract not necessary for the immunogenicity. It is advantageously carried out several times with phosphate buffers or a saline solution of increasing concentration. Thus, the first wash is carried out with a phosphate buffer or a solution of NaCl having a concentration of less than or equal to 200 mM, whereas a second wash may be carried out with a phosphate buffer or a solution of NaCl having a concentration of between 300 and 500 mM.

In practice, the step for preparing the tumor extract is advantageously carried out in the following way:
  optionally, freezing of the tumor tissue,
  grinding of the tumor tissue,
  solubilization or suspension of the cytoplasmic tumor antigens in a solution of $NaHCO_3$,
  centrifugation,
  separation of the pellet and of the supernatant.

Still in practice, when the method for preparing tumor antigens implements the additional step of mixing the tumor antigens that have been purified and adsorbed onto the microparticulate mineral support, with a cofactor, said cofactor is advantageously prepared from the centrifugation pellet obtained during the preparation of the tumor extract. Thus, said pellet is suspended, and it is subjected to a step aimed at separating the membrane fraction by centrifugation in a sugar gradient, preferably a sucrose gradient, the membrane fraction comprising the cofactor thus purified being recovered.

The method according to the invention is based on the demonstration by the inventors of the advantage of certain specific supports. Thus, the particulate mineral support according to the invention has surface properties which allow, including without a coupling agent, the specific binding of the active substances, in particular of the biological agent, and more particularly of tumor antigens, and their transport to cells of the mononuclear phagocyte system. For this, the particulate mineral support is chosen from minerals having all or some of the following properties: presence of at least one of the ionized or ionizable groups $PO_4^{2-}$, $OH^-$ and/or $Ca^{2+}$ at the surface of said material, basic surface pH, negative electrokinetic potential and/or hydrophobic. Such compounds can be chosen from the group comprising calcium minerals, preferably calcium phosphates, and even more preferably hydroxyapatites. The microparticulate mineral support of choice corresponding to the abovementioned features is chosen from ceramics, and especially a calcium phosphate ceramic, in particular a hydroxyapatite, or a tricalcium, tetracalcium or octocalcium phosphate in particulate form.

Ceramics are a material of choice for the implementation of the method according to the invention; in fact, calcium phosphates which have undergone a calibrated thermal treatment are more suitable for bringing into contact, and particularly percolating, ground tissue material than calcium phosphates directly derived from synthesis without treatment. The ground tissue materials contain in particular fibrins, which are capable of polymerizing in the presence of calcium and therefore of clogging a column comprising such a support.

Such a support under certain shape and particle size conditions allows the percolation of a ground tumor material in a column without clogging of said column.

The invention is, moreover, also partly based on the observation that these microparticles which have adsorbed active substances, or are capable of doing so, are "phagocytable", when the size of said microparticles is sufficiently small, by cells belonging to the mononuclear phagocyte group which comprises macrophages, dendritic cells and other antigen-presenting cells (APCs). Another inventive observation made by the inventors is that the introduction, in vivo, of these particles of phagocytable size into the subcutaneous tissue attracts cells of the mononuclear phagocyte system, and in particular antigen-presenting cells (APCs), which become concentrated at the site where the microparticles of the medicament according to the invention are located, and which phagocytose said microparticles.

Thus, the size of the particles of the particulate mineral support is an important feature of the invention. According to a preferred arrangement, it is a good idea for the particle size of the particulate mineral support to be less than or equal to 200 µm, preferably less than or equal to 90 µm, and even more preferably less than or equal to 50 µm, entirely preferably between 10 and 50 µm, ideally less than 10 µm, and with a specific surface area of between 0.1 and 5 $m^2/g$, preferably between 0.3 and 2 $m^2/g$. It is important to specify that, due to the degradability of the support and to its structure, the particles will become fractionated into microparticles of smaller size once injected into the patient.

The term "particle size" is intended to mean the average size of the particles, and more specifically average size of the largest dimension of nonspherical particles or diameter for spherical particles. The methods for measuring the particle size are conventional, for example by laser diffraction.

These particle size features relate more especially, but not limitingly, to pulverulent solid supports, preferably based on hydroxyapatite.

The shape of the particles is also important; in fact, spherically shaped particles are particularly suitable for the implementation according to the invention, unlike needle-shaped particles.

According to one variant, the method according to the invention comprises an additional step carried out after the purification and the binding to the support according to the invention, and according to which the tumor antigens are desorbed in a solution of NaCl or a phosphate buffer at 500 mM, which is then diluted to between 100 and 200 mM and again passed over a column comprising a support as defined in claims 10 to 13 having a particle size of less than 10 µm.

According to one variant, the solid support may be nonpulverulent. In such a case, it may, for example, be a ceramic capable of degrading in vivo by dissolution of the grain joints and release of particles consisting of a varying number of grains. When their size is less than or equal to approximately 200, or even 90, and even better still 50 µm, the particles are phagocytable by macrophages and giant cells which accumulate in the degradation zones of the ceramic.

The solid support (for example, ceramic) may, after having been degraded in the form of grains, penetrate into the cells by pinocytosis, endocytosis and phagocytosis that can transport biological molecules, and in particular tumor antigens and adjuvant factors.

The solid support may, for example, be composed of the combination of a ceramic and of one or more biocompatible, degradable polymers. It may also be a solid as described, with at its surface, organic molecules for binding antigens to the surface and/or targeting certain cell types.

The adsorbable or adsorbed biological materials such as antigens are advantageously chosen from constituents of tumor cells, molecules, organelles, cell conversion products (e.g. ground materials, lyophilizates, dialysates, centrifugation pellet, etc.) and also constituents of viruses, bacteria, endotoxins, and mixtures thereof.

Preferably, the antigens, preferably tumor antigens— which may be natural or synthetic, and which may or may not be modified chemically and/or physically and/or genetically, inter alia—are selected from membrane antigens, cytoplasmic antigens, extracellular antigens, and mixtures thereof.

The adsorbable or adsorbed biological molecules are advantageously chosen from the following group of adjuvant factors: proteins—preferably heat shock proteins (HSPs), —nucleic acids, lipids, phospholipids, carbohydrates and glycoproteins.

These HSPs are in particular but not exclusively gp96, hsp70, hsp90 and hsp100. The active substances adsorbed or adsorbable onto the biocompatible support may also comprise genes encoding the biological molecules and/or materials as defined above, preferably encoding tumor antigens and/or adjuvant factors—preferably cytokines and/or lymphokines—for activating the antibody—presenting cells (APCs).

Preferably, the active substances may comprise tumor antigens and/or genes encoding tumor antigens, and more particularly heat shock proteins (HSPs). The biological molecules are thus, for example, tumor antigens which may or may not be associated with HSPs.

Entirely preferably, the tumor antigens are chosen from:
antigens whose expression is shared in various histological types of cancers, and more particularly the antigens MAGE (melanoma antigens), BAGE (bladder antigens), GAGE (gastric antigens), RAGE (renal antigens), α-fetoprotein, MUC1, HER-2/neu, and mixtures thereof,
antigens encoded by mutated genes, and more particularly the ras oncogenes, the suppressor genes p53, β-catenin and Cdk4, the bcr/ab1 antigen fusion, products of viral genes (Epstein Barr, hepatitis B, papilloma), CASP-8, and mixtures thereof,
the tumor-associated antigens carcinoembryonic antigen, prostate antigen, RU2, Alt-M-CSF, tyrosinase, melan-A/MART1, Gp100, Gp75, Glioma associated oncogene, GLIP1, and/or
heat shock proteins (HSPs), preferably the gp96 protein and the associated peptides.

The invention also relates to a medicament, preferably an autovaccine, characterized in that it comprises tumor antigens obtained by means of the method described above.

Thus, the medicament according to the invention comprises at least one biocompatible solid support, preferably in powder form, onto which is adsorbed or onto which is intended to be adsorbed, preferably without requiring a coupling agent, at least one active substance, preferably chosen from the biological materials comprising the group of antigens contained in tumor cells, their cellular organelles, their membranes, their conversion products (ground materials, lyophilizates, dialysates, centrifugation pellet, etc.), viruses, bacteria, antibodies, endotoxins, and mixtures thereof, said biocompatible support having been used to purify said active substance.

The term "medicament" should be understood to mean that the medical devices comprising, for example, a mineral powder and at least one active substance are also covered. The term "coupling agent" refers to a chemical fraction which covalently links the biocompatible solid support and the active substance. It may in particular involve a covalent bond or an organic radical.

The invention is in part based on the observation that these microparticles having adsorbed active substances or capable of doing so are "phagocytable", when the size of said microparticles is sufficiently low, by cells belonging to the group of mononuclear phagocytes which comprises macrophages, dendritic cells and other antigen-presenting cells (APCs). Another inventive observation made by the inventors is that the introduction, in vivo, of these particles of phagocytable size into the subcutaneous tissue attracts cells of the mononuclear phagocyte system, and in particular APCs, which become concentrated at the site where the microparticles of the medicament according to the invention are located, and which phagocytose said microparticles.

The inventors have demonstrated the fact that a molecule adsorbed onto a particle, for example of HA, of phagocytable size, penetrates rapidly, for example, into APCs. Without being limiting, this rapid penetration may be explained in two ways: either the adsorbed molecule is directly released into the cell after having been phagocytosed with the support particle, or this molecule is desorbed and released in the immediate vicinity of the cell and penetrates therein in a second step.

For example, when the HSP heat shock protein gp 96 is bound to the HA particles, it can be released therefrom by means of a solution of calcium phosphate titrated at 200-300 mM, which is a concentration encountered in vivo in intracellular and extracellular fluids.

Advantageously, this medicament can be used for autologous treatments by immunotherapy, in particular as a vaccine, preferably as an antitumor vaccine.

According to a notable embodiment of the invention, the tumor antigens are prepared from the patient's tumor, the medicament then being an autovaccine.

According to one of the particularly surprising embodiments of the invention, the medicament comprises tumor antigens adsorbed onto a particulate mineral support having been used for the purification of said antigens from a tumor extract.

The active substances, biological materials and, more particularly, the tumoral agents adsorbable or adsorbed onto the biocompatible support and which constitute in part the medicament according to the invention are those which have been defined above.

In another implementation of the invention, the medicament may comprise, in addition to the tumor proteins adsorbed onto the microparticulate mineral support, a cofactor, said cofactor preferably being in the form of tumor extracts, in particular of ground materials, lyophilizates, dialysates or a centrifugation pellet. Entirely preferably, the cofactor originates at least in part from a tumor extract, and more particularly from the tumor extract from which the targeted tumor proteins were purified by adsorption onto the particulate mineral support.

The medicament according to the invention comprises biocompatible solid particles, preferably of calcium phosphates, which surprisingly and unexpectedly have the property of stimulating the growth and the effectiveness of macrophages and/or other APCs, such as dendritic cells.

The invention is therefore also directed toward a medicament characterized in that it is intended to activate macrophages and/or other APCs, i.e. to bring about the synthesis of substances chosen from the group comprising cytokines, lymphokines and growth factors, and/or to render dendritic cells mature.

Another advantageous feature of the medicament stems from the fact that it is intended to be phagocytosed by macrophages and/or other APCs and/or dendritic cells.

The medicament according to the invention is also notable in that it allows the in vivo transport of one or more active substances.

In other words, the solid support (for example, calcium phosphates, in powder form or not—in bulk, —ceramic or not) according to the invention makes it possible to vectorize any adsorbable substance/molecule using antigen-presenting cells (APCs) or other similar cells.

As regards it use, the medicament according to the invention is characterized in that it can be implanted in vivo and/or administered by injection.

According to advantageous mode, the medicament according to the invention allows the sustained release (for example for a few hours to several days), in vivo, of the adsorbed active substance(s).

Once injected into a connective tissue, the medicament according to the invention can bring about a local afflux of macrophages, dendritic cells and/or other APCs for presenting the antigen(s) adsorbed onto the support.

The adsorption of the active substance(s) onto the solid support according to the invention can take place in vivo and/or ex vivo, this support being a powder, preferably hydroxyapatite as defined above.

Thus, a medicament comprising a solid support in powder form according to the invention allows a ground tumor material to be percolated through a column of said support and said powder to be injected into the subcutaneous tissue or alternatively the lymph nodes.

In practice, the medicament according to the invention comprises tumor antigens, the amount of which is directly proportional to the specific surface area of the powder. Preferably, the medicament comprises tumor antigens in an amount of 20 mg/g of mineral support powder.

When it is used in the form of a galenical unit, the medicament according to the invention is advantageously used in an amount of between 15 and 100 µg dose/galenical unit.

The solid support used in the medicament according to the invention can at the same time be used for purifying active substances, immobilizing active substances at the surface of said support, injecting/implanting and releasing active substances into and in the organism, or conveying biological active substances into APCs or other similar cells.

A subject of the invention is also the use of the biocompatible support solid, preferably in powder form, as defined above, and optionally of at least one active substance also defined above, for preparing a medicament as defined above.

Another subject of the invention is directed toward a method for preparing a medicament, in particular as described above, characterized in that it consists essentially in bringing at least one biocompatible solid support, preferably in powder form, into contact with at least one active substance, preferably chosen from biological materials and/or biological molecules, in such a way that the active substance reversibly adsorbs onto the support.

Preferably, this method is characterized in that it comprises the purification of possibly autologous active substances that can be used to bring about an immunotherapy, this method comprising the following essential steps:

bringing the active substance(s) into contact with a calcium phosphate powder for a period of time sufficient for the immobilization/adsorption of at least a part of the active substance(s)—preferably at least one immune factor and/or at least one adjuvant factor—on/onto the powder to take place;

recovering the powder having immobilized at least a part of the active substance(s), in order to prepare a medicament that can be administered to a patient suffering, for example, from a cancer, an infectious disease or an autoimmune disease, this or these active substance(s) possibly originating from the patient in the case of an autologous treatment.

In one variant, this method is characterized in that it comprises the purification of autologous factors that can be used to bring about an antitumor immune reaction, this method comprising the following essential steps:

bringing a ground tumor material into contact with a calcium phosphate powder for a period of time sufficient for the immobilization of certain molecular factors—preferably at least one immune factor and/or at least one adjuvant factor—on the powder to take place;

washing the powder with one or more saline solutions of various molarities and/or pHs so as to remove the non-adsorbed molecules;

recovering the powder having immobilized certain molecular factors in order to prepare a medicament that can be injected into the body of the individual suffering from the tumor from which the ground material is extracted.

In practice, the bringing into contact may, for example, be a purification carried out using one or more columns which may or may not be separated by a reservoir system into which or from which certain solutions can be introduced or withdrawn, and through which column(s) a ground tumor material can be percolated.

Still in practice, the recovery of the active substance(s) may, for example, be carried out by elution of the column(s) by means of a buffer solution—preferably a phosphate buffer solution—of appropriate molarity and pH, the eluate thus obtained comprising tumor antigens and/or the adjuvant factors that were immobilized and were sought. This is a chromatography technique.

Insofar as it does not involve chromatography, the recovery of the active substance(s) is carried out by recovery of the powder having adsorbed the tumor antigens and/or the adjuvant factors that were immobilized and were sought.

By virtue of the selective adsorption properties of the solid support used according to the invention, it is possible to perform an assay of adsorbed active substances after desorption.

This assay may, for example, be carried out by purification of the specific surface area of the support measured by gas adsorption (BET measurement). However, all the known analytical methods may be envisioned.

In order to illustrate this capacity for selective adsorption, it may be pointed out that gp96, for example, binds to the surface of the HA particles at low phosphate buffer molarities. It is desorbed from the powders at between 200 mM and 300 mM.

The invention is directed toward, in addition and inter alia:
a method for preparing a medicament, characterized in that it comprises the method for preparing tumor antigens as described above. Preferably, this method uses a tumor extract prepared from the patient's tumor, said medicament being an autovaccine. According to a specific embodiment of said method, the purified tumor antigens adsorbed onto the particulate support, optionally mixed with at least one cofactor, are in the form of an injectable preparation;

a method for purifying biological molecules/materials of the type of those defined above, and in particular heat shock proteins HSPs and/or antitumor antigens, consisting in using the solid support as defined above as a selective adsorption/desorption means;

a purification system containing a powder defined above, and consisting of one or more columns which may or may not be separated by a reservoir system into which and from which certain solutions can be introduced or withdrawn, and which makes it possible, based on the introduction of a ground tumor material into the system, to obtain, at the outlet, an injectable powder onto which tumor antigens and/or adjuvant factors have been adsorbed.

This purification system advantageously comprises a system for introducing the powder into the organism, which is removable and which makes it possible to inject it or to project it into the patient's subcutaneous tissue;

therapeutic methods consisting in administering the medicament according to the invention for the treatment and/or prevention in particular of cancers, of infectious diseases or of autoimmune diseases;

therapeutic methods consisting in administering the medicament according to the invention for the treatment and/or prevention, by immunotherapy (for example autologous), in particular of cancers, of infectious diseases or of autoimmune diseases;

and autologous vaccines comprising the medicament according to the invention for the treatment and/or prevention in particular of cancers, of infectious diseases or of autoimmune diseases.

It emerges in particular from the above disclosure of the invention that the HA particles are a good vector for transporting heat shock proteins into macrophages and antigen-presenting cells, as shown by the following examples.

FIG. 1: antigen presentation by APCs to the effector cells of the immune reaction, T lymphocytes.

Figure 2:
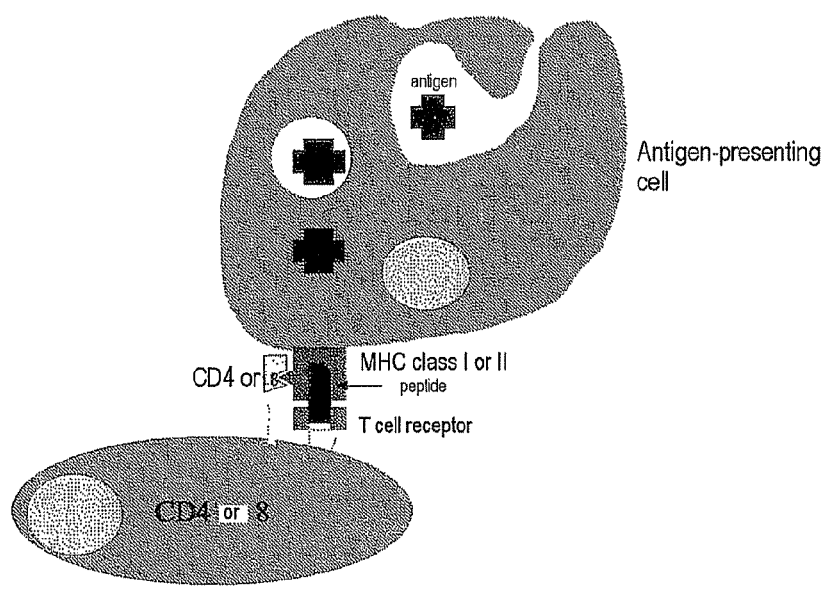

FIG. 2: once phagocytosed, the antigen is fragmented into peptides which are associated with the MHC so that they can be recognized by the lymphocytes.

Figure 3A:
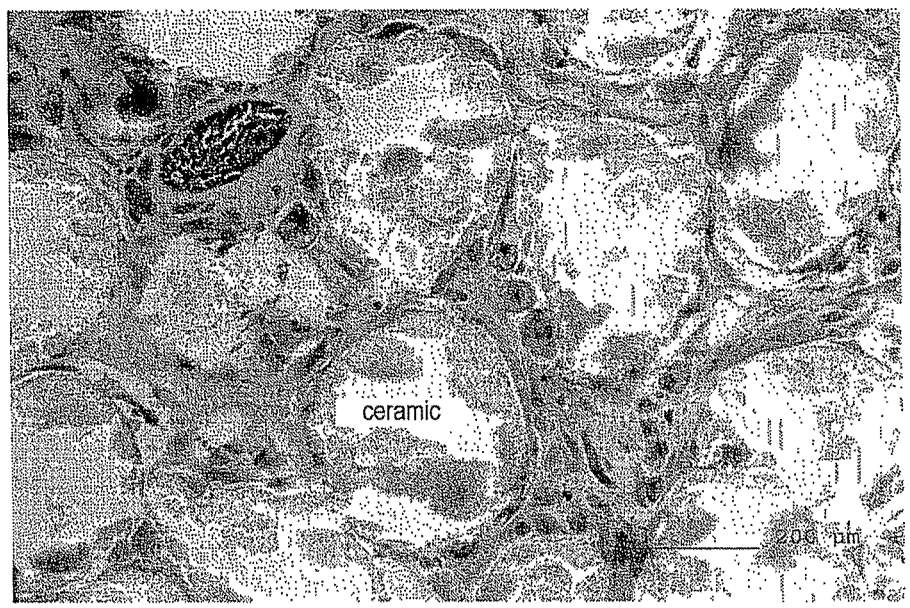

FIG. 3A: histological section of calcium phosphate particles, implanted in a rabbit mandible, carrying a vector plasmid for a Lac-Z gene, showing an accumulation of macrophages and of APCs around the particles.

Figure 3B:
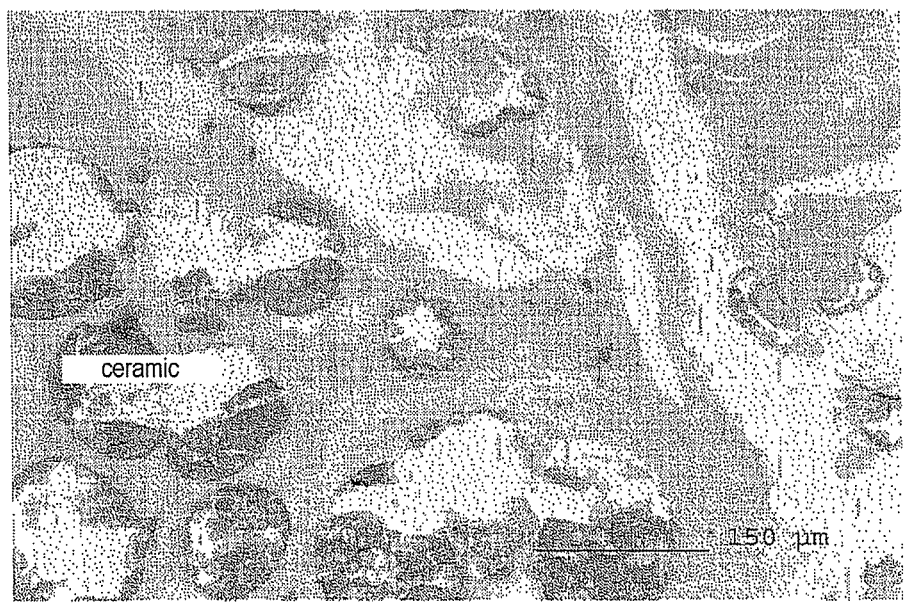

FIG. 3B: histological section of calcium phosphate particles, implanted into a rabbit mandible, carrying a plasmid vector for a Lac-Z gene, showing an accumulation of macrophages and of APCs around the particles. The visualization of the galactosidase activity shows that all the cells in proximity are transfected.

Figure 4:
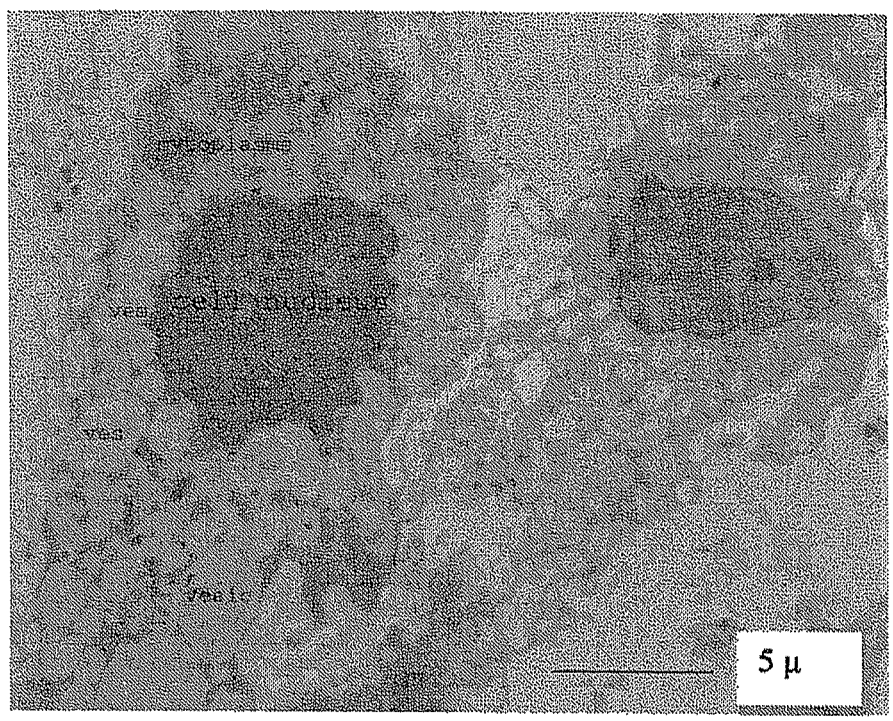

FIG. 4: transmission electromicroscopy section of medullary cells cultured in contact with HA particles after demineralization. There are a large number of empty cytoplasmid vesicles which contained the particles before they were dissolved.

Figure 5:
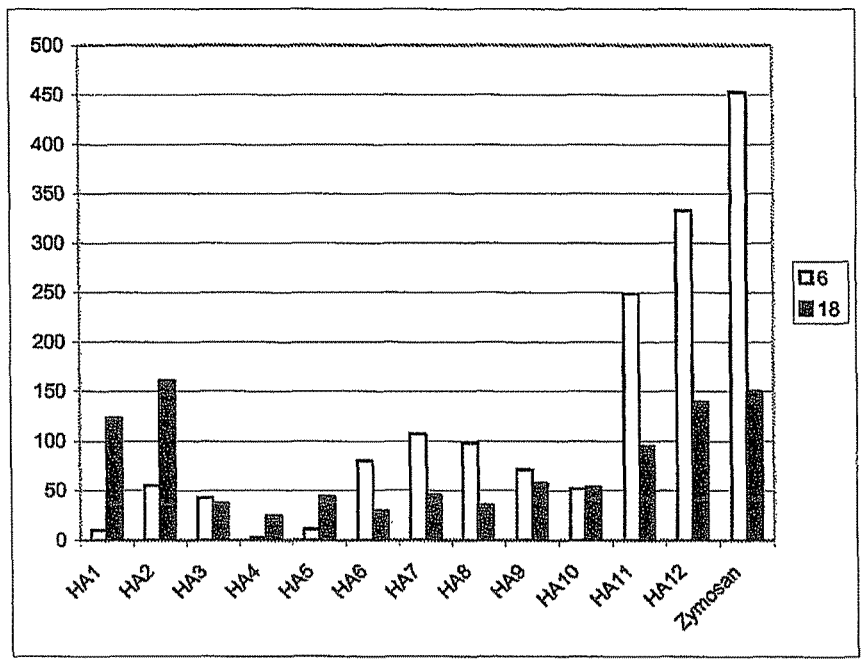

FIG. 5: TNF-α mRNA/β-actin mRNA.

Figure 6:
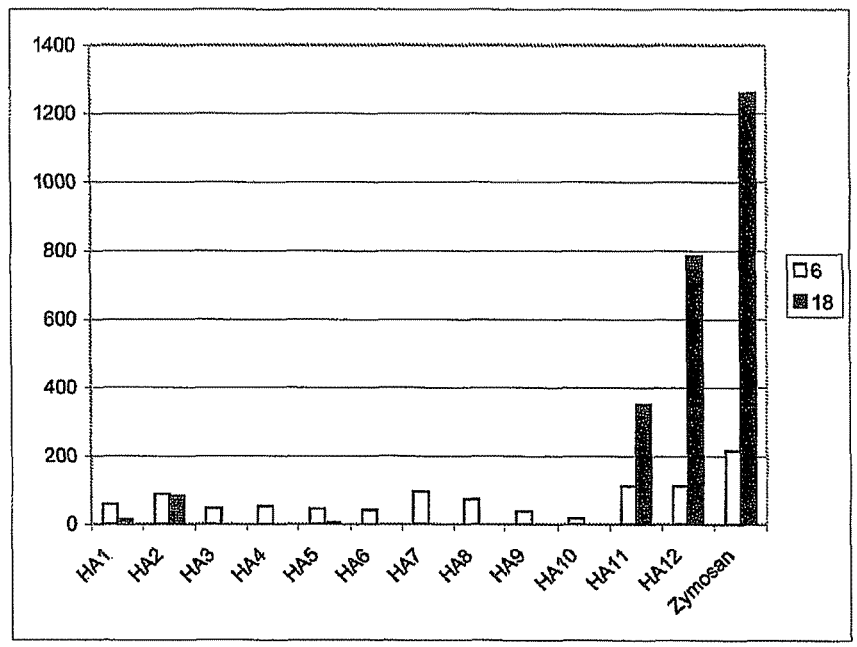

FIG. 6: IL-6 mRNA/β-actin mRNA.

Figure 7:
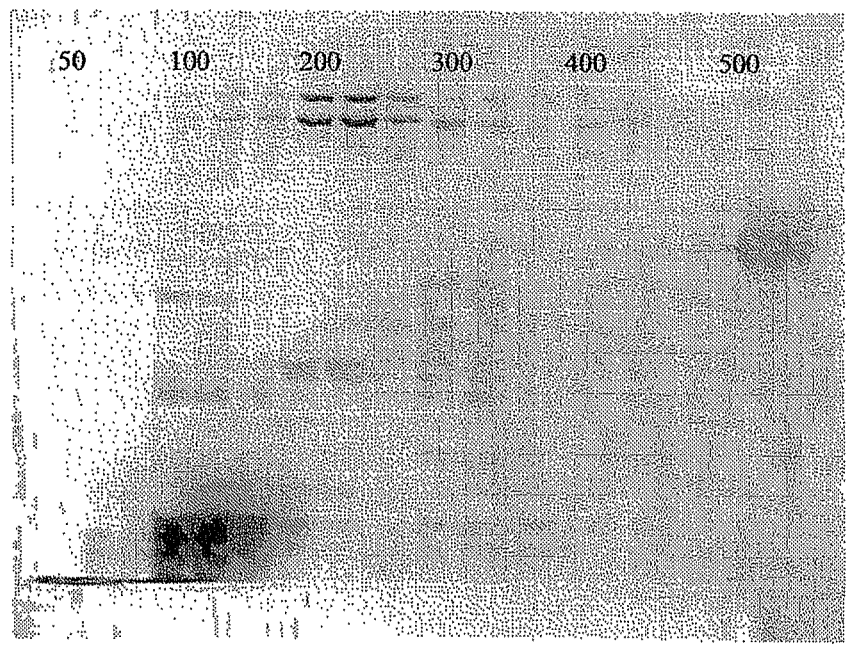

FIG. 7: slot blot of various fractions of ground tumor materials, collected at the exit of an HA column. The fraction obtained by washing with 200 mM of phosphate buffer shows the best yield of gp96 (HSP) (black bar at the top of the electrophoresis).

Figure 8:
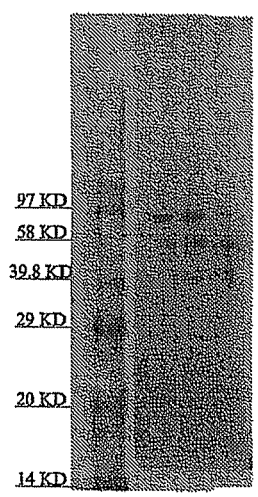

FIG. 8: western blot of the 200 mM fraction.

EXAMPLE 1

Capacity of HA Particles for Intracellular Transport of Biological Molecules into Macrophages and Giant Cells 2 mg of HA particles are used in this experiment. The characteristics of the powder are the following: particle size 45-80 μm; specific surface area: 0.7 m$^2$/gr; spherical shape; negative surface charge, surface potential −37 mV, hydrophobic. A plasmid carrying a galactosidase gene (Lac-Z) is adsorbed to the surface of the powders according to the following protocol: 25 μg of plasmid are diluted in 2 ml of 0.1M phosphate buffer, pH 6.8. The powder is incubated for two hours in the plasmid solution at 37° C. and then dried.

The 2 mg of powder are implanted in a bone defect made by the junction of the incisor ligament of rabbit mandibles. The animals are sacrificed at three weeks and the mandibles are removed. Histological sections are cut and the glactosidase activity of the cells is revealed by means of the GalX reaction, before observation by optical microscopy.

There is an accumulation of macrophages and giant cells around the particles of powder (FIGS. 3A and 3B). All the cells at the periphery of the powders have a galactosidase activity, which suggests that the plasmid has migrated from the surface of the powders into the nucleus of the macrophages. Fragments of particles are visible in the cytoplasms, which indicates that they have been phagocytosed. There are numerous mononuclear or multinuclear cells expressing the lac-Z gene, which have migrated to the surface of the trabeculae, at a distance from the particles.

This experiment shows that:
the DNA immobilized at the surface of the HA particles is preferentially transported into the cells which present the antigen.
these cells migrate with the molecules that they contain.

EXAMPLE 2

Degradation of the Particles of Powder 10 mg of sterile powders with the characteristics of Example 1 are introduced into a culture flask which contains a confluent layer of a primary human medullary cell line. The cells are cultured in contact with the powders in a DMEM medium supplemented with 10% fetal calf serum and glutamine at 37° C. in a 5% $CO_2$ atmosphere for 4 hours. They are then examined by optical microscopy. They show an acid phosphatase activity indicating that these cells belong to the mononuclear phagocyte system. Numerous ceramic particles or fragments are in contact or are included in the cytoplasm. The cells are then fixed in a 4% glutaldehyde solution, demineralized in a solution of EDTA, and embedded in an epoxy polymer. Sections of 200 angstroms are cut and examined by transmission electron microscopy. There is a very large number of empty vesicles in the cell cytoplasm, which indicate the position of the particles before demineralization (FIG. 4).

It is therefore established that the HA particles degrade, emitting grains which are phagocytosed by the antigen-presenting cells.

EXAMPLE 3

Activation of APCs by the Particles

Various hydroxyapatite particles are introduced into a culture flask containing a primary human monocyte line before confluence. The cells are in contact with the powders, the characteristics of which are given in Table 2, for 6 or 18 hours. The cell density when the culture dishes are seeded is 2×10$^5$ cells/ml. The culture medium is RPMI-1640 supplemented with 10% fetal calf serum. The cells are cultured at 37° C. and in a 5% $CO_2$ atmosphere. The mass of powder introduced into the culture is the mass necessary for the cell surface/powder surface ratio to be equal to 1. The amounts of TGF-β mRNA and of IL-6 mRNA are assayed at 6 and 18 hours (FIGS. 5 and 6).

TABLE 2

| | Powder characteristics | | | | | | | | | | | |
|---|---|---|---|---|---|---|---|---|---|---|---|---|
| | HA1 | HA2 | HA3 | HA4 | HA5 | HA6 | HA7 | HA8 | HA9 | HA10 | HA11 | HA12 |
| Particle size (μm) | 1-30 | 1-30 | 10-70 | 110-190 | 170-300 | 1-30 | 1-30 | 1-30 | 100-250 | 150-300 | 1-30 | 1-30 |
| Average | 3 | 3 | 44 | 140 | 217 | 3 | 3 | 3 | 166 | 196 | 2 | 2 |

TABLE 2-continued

| | | | | | | Powder characteristics | | | | | | |
|---|---|---|---|---|---|---|---|---|---|---|---|---|
| | HA1 | HA2 | HA3 | HA4 | HA5 | HA6 | HA7 | HA8 | HA9 | HA10 | HA11 | HA12 |
| size (μm) Sintering (° C.) | 600 | 1180 | 1180 | 1180 | 1180 | 20 | 600 | 1180 | 1180 | 1180 | 20 | 600 |
| Specific surface area ($m^2g^{-1}$) | 23.95 | 5.38 | 1.56 | 0.63 | 0.5 | 38.06 | 26.72 | 6.08 | 0.7 | 0.7 | 18.51 | 13.18 |
| Grain size (nm) | 190 | 350 | 350 | 350 | 350 | 80 | 180 | 350 | 420 | 350 | 200 | 300 |
| Shape (1) | S | S | S | S | S | A | A | A | A | A | N | N |

(1) Grain shape: S = sphere; A = any; N = needle

The results show that the characteristics of the hydroxyapatite particles influence their ability to cause the APCs that have phagocytosed them to synthesize interleukins and TGF-β, i.e. their ability to activate them. The needle-shaped particles are the most inflammatory. As regards the other shapes, the smallest particles are the most inflammatory. It is known that particles of HA powder degrade during their tissue implantation and that smaller debris are emitted, which makes it possible to amplify the activation of the macrophages.

EXAMPLE 4

Purification of Gp96 Heat Shock Proteins on Beds of Injectable HA Power

The purification is carried out according to the following steps:
Preparation of the Support:
10 g of powder are rehydrated for eight hours in a phosphate buffer of low ionic strength (0.01M, pH 6.8) at ambient temperature in a volume equal to 4 to 5 times the volume of the powder. The excess buffer is removed with the particles which have not sedimented. The powder is resuspended in an excess of buffer, and poured into the column, the lower end of which is closed. It is left to separate by settling out for a few hours and the buffer is then removed by the bottom of the column. The column is then equilibrated in a phosphate buffer (0.01M, pH 6.8). The column is then washed in a 30 mM phosphate buffer, pH 6.8 (20-30 times the column volume).
Percolation of the Suspension Through the Column Containing the HA:
The protein load (precipitate of the ground tumor material to which 30 mM phosphate buffer, pH 6.8, has been added in a 1/10 proportion) is introduced into the column.
Washing of the Column:
The column is then washed with a phosphate buffer gradient of from 0 to 500 mM.
The support and the protein fractions are collected.

EXAMPLE 5

Control of the Protein Fractions Obtained by Fractionation on an HA Column with Various Phosphate Buffer Molarities Two controls of the various fractions were carried out, by slot blot electrophoresis and western blotting methods, which are well known methods. The results of the electrophoresis show that the majority of the gp96 proteins detach from the HA at 200 mM. The western blotting shows that the protein fraction is virtually pure at this molarity (FIGS. 7 and 8).

EXAMPLE 6

Preparation of an Autovaccine

All the following manipulations are carried out under sterile conditions.
1. Preparation of the Tumor Tissue and Freezing
The tumor tissue is removed (approximately 1 $cm^3$) during a biopsy carried out under sterile conditions, and immediately frozen.
2. Grinding of the Tumor Extract
The tumor tissue is ground in a mortar and the fragments are then transferred into a Kahn tube on a bed of ice.
3. Dilution of the Ground Material in a Solution of $NaHCO_3$
The ground material obtained in step 2 is mixed with 750 μl of 30 mM $NaHCO_3$, pH 7. The tissue is then homogenized with a knife mill.
4. Separation of the Pellet and of the Supernatant by Centrifugation
The homogenate is transferred into an Eppendorf tube and centrifuged at between one and two thousand g for 30 min at 4° C. Two fractions are then obtained, one of them corresponds to the supernatant comprising the tumor proteins in suspension and in solution, the other corresponds to the pellet and comprises the membrane fractions.
5. Percolation of the Suspension Over a Hydroxyapatite (HA) Column
Preparation of the Column:
A column of HA powder is prepared: the powder is suspended in a phosphate buffer (20 mM, pH 7), and left to sediment for 30 seconds, and the supernatant is discarded in order to remove the fine particles in suspension that are liable to clog the column during the passing of the protein solution. The column is then washed with 10 times the volume represented by the powder, with a phosphate buffer solution.
Percolation of the Supernatant Over the HA Column:
The proteins of the supernatant obtained in step 4 are precipitated using an ammonium sulfate solution and the precipitate is taken up in a solution of phosphate buffer in which the proteins are solubilized or in suspension. The solution containing the tumor proteins that are in suspension and solubilized is percolated over a bed of ceramics in order to recover the heat shock proteins (gp96).
6. Washing of the Column
When the solution of proteins has penetrated into the bed of HA, the column is washed with 4 to 5 times its volume of phosphate buffer (20 mM, pH 7). The column is then washed with a gradient of phosphate buffer or of calcium chloride of 0-200 mM, of 4 to 5 times the volume of the powder.

7. Preparation of the Cofactor

The pellet obtained in step 4 is resuspended in 400 µl of phosphate buffer (20 mM, pH 7).

A sucrose gradient is prepared in 400 µl sections of 40%, 35% and 30%, on which gradient 200 µl of the pellet obtained in step 1 will be deposited. The gradient thus loaded with tumor extract will then be centrifuged at 1500 g for 30 min at 4° C. The fraction containing the membrane fragments, located at the 40% sucrose/35% sucrose interface, is recovered.

8. Preparation of the Mixture to be Injected

The powder in suspension that has adsorbed the proteins from the supernatant obtained at the end of step 4 is then combined with the solution of membranes obtained in step 3 (20 mg per 100 µl). The mixture is then introduced into a syringe, where the volume of the mixture is optionally adjusted through the addition of a solution of NaCl (9/1000).

The invention claimed is:

1. A method for preparing an antitumor vaccine, comprising:
   a. obtaining tumor tissue from a patient;
   b. grinding the tumor tissue;
   c. solubilizing or suspending cytoplasmic tumor proteins of the ground tumor tissue to form an extract;
   d. centrifuging the extract to yield a membrane fraction and a supernatant containing the cytoplasmic tumor proteins;
   e. combining the supernatant with powdered ceramic hydroxyapatite to form loaded hydroxyapatite; and
   f. washing the loaded hydroxyapatite with a buffer solution to recover a composition comprising cytoplasmic tumor proteins adsorbed onto powdered ceramic hydroxyapatite
   wherein said powdered ceramic hydroxyapatite consists of a powder of spherically shaped particles of hydroxyapatite having the following characteristics:
      a particle size between 1-30 µm, and
      having been exposed to a sintering temperature of 600° C.

2. A composition comprising cytoplasmic tumor proteins adsorbed on powdered ceramic hydroxyapatite, wherein the powdered ceramic hydroxyapatite is a powder of spherically shaped particles of hydroxyapatite having the following characteristics:
   a particle size between 1-30 µm, and
   having been exposed to a sintering temperature of 600° C.

3. A composition according to claim 2, obtained by the following steps:
   a. obtaining tumor tissue from a patient;
   b. grinding the tumor tissue;
   c. solubilizing or suspending cytoplasmic tumor proteins of the ground tumor tissue to form an extract;
   d. centrifuging the extract to yield a membrane fraction and a supernatant containing the cytoplasmic tumor proteins;
   e. combining the supernatant with powdered ceramic hydroxyapatite to form loaded hydroxyapatite; and
   f. washing the loaded hydroxyapatite with a buffer solution to recover a composition comprising cytoplasmic tumor proteins adsorbed onto powdered ceramic hydroxyapatite; said powdered ceramic hydroxyapatite consisting of a powder of spherically shaped particles of hydroxyapatite having the following characteristics:
   a particle size between 1-30 µm, and having been exposed to a sintering temperature of 600° C.

4. A method for preparing an antitumor vaccine, comprising:
   a. obtaining tumor tissue from a patient;
   b. grinding the tumor tissue;
   c. solubilizing or suspending cytoplasmic tumor proteins of the ground tumor tissue to form an extract;
   d. centrifuging the extract to yield a membrane fraction and a supernatant containing the cytoplasmic tumor proteins;
   e. combining the supernatant with powdered ceramic hydroxyapatite to form loaded hydroxyapatite; and
   f. washing the loaded hydroxyapatite with a buffer solution to recover a composition comprising cytoplasmic tumor proteins adsorbed onto powdered ceramic hydroxyapatite; said powdered ceramic hydroxyapatite consisting of a powder of spherically shaped particles of hydroxyapatite having the following characteristics: a particle size between 1-30 µm, and having been exposed to a sintering temperature of 600° C.

5. A composition cytoplasmic tumor proteins adsorbed on powdered ceramic hydroxyapatite obtained by the method of claim 1.

6. An antitumor vaccine obtained by the method of claim 4.

* * * * *